US012678054B2

(12) United States Patent (10) Patent No.: US 12,678,054 B2

Al Waked (45) Date of Patent: Jul. 14, 2026

(54) ADJUSTABLE DENTAL IMAGING DEVICE

(71) Applicant: Imam Abdulrahman Bin Faisal University, Dammam (SA)

(72) Inventor: Jamal Al Waked, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 155 days.

(21) Appl. No.: 18/892,309

(22) Filed: Sep. 20, 2024

(65) Prior Publication Data

US 2025/0009234 A1 Jan. 9, 2025

Related U.S. Application Data

(63) Continuation of application No. 18/766,721, filed on Jul. 9, 2024, now Pat. No. 12,161,441, which is a continuation of application No. 18/623,386, filed on Apr. 1, 2024, now Pat. No. 12,059,231, which is a continuation of application No. 17/319,771, filed on May 13, 2021, now Pat. No. 11,980,445.

(51) Int. Cl.
*A61B 5/00* (2006.01)

(52) U.S. Cl.
CPC .......... *A61B 5/0088* (2013.01); *A61B 5/0077* (2013.01); *A61B 5/70* (2013.01)

(58) Field of Classification Search
CPC ..................... A61B 5/0088; G03B 17/56–566
See application file for complete search history.

(56) References Cited

U.S. PATENT DOCUMENTS

| | | | |
|---|---|---|---|
| 2,314,033 | A | 3/1943 | Curran |
| 5,332,136 | A | 7/1994 | Rudolph |
| | | (Continued) | |

FOREIGN PATENT DOCUMENTS

| | | |
|---|---|---|
| BR | 102015031353-5 A2 | 6/2017 |
| JP | 2006-334241 A | 12/2006 |
| KR | 20170142431 A | 12/2017 |

OTHER PUBLICATIONS

Freedman ; Standardization in dental photography ; Article in Compendium (Newton, PA) ; Jan. 1990 ; 3 Pages.

(Continued)

*Primary Examiner* — Leon W Rhodes, Jr.
(74) *Attorney, Agent, or Firm* — Oblon, McClelland, Maier & Neustadt, L.L.P.

(57) ABSTRACT

A dental and facial imaging device includes an adjustable arm, an image sensor mounted on a first end of the adjustable arm and an adjustable patient positioning arm mounted on a second end of the adjustable arm. A distance between the adjustable patient positioning arm and the image sensor is adjustable based on an adjustable length of the adjustable arm. A position indicator scale of the adjustable arm includes multiple notches for calibrating the distance between the adjustable patient positioning arm and the image sensor. The adjustable patient positioning arm includes a patient teeth supporting device and a patient chin rest which are positioned at a fixed coordinate reference relative to the image sensor to capture an image of a patient's teeth. The fixed coordinate reference corresponds to co-ordinates of multiple anatomical planes associated with the patient teeth supporting device and a patient chin rest relative to the image sensor.

18 Claims, 10 Drawing Sheets

(56)                         References Cited

U.S. PATENT DOCUMENTS

| | | | |
|---|---|---|---|
| 5,388,580 | A | 2/1995 | Sullivan |
| 7,703,995 | B1 | 4/2010 | Sivan |
| 8,992,217 | B2 | 3/2015 | Cho |
| 9,675,419 | B2 | 6/2017 | Akeel |
| 10,543,065 | B2 | 1/2020 | Lin |
| 10,561,315 | B2 | 2/2020 | Myung |
| 10,779,718 | B2 | 9/2020 | Meyer |
| 11,422,438 | B2 * | 8/2022 | Lai ......................... H04N 23/50 |
| 2010/0025444 | A1 | 2/2010 | Tipton |
| 2010/0217130 | A1 | 8/2010 | Weinlaender |
| 2015/0346590 | A1 | 12/2015 | Lewis |
| 2020/0297205 | A1 | 9/2020 | Hill |

OTHER PUBLICATIONS

Brouwer, et al. ; Standardized Intraoral Photography ; Journal of Clinical Orthodontics ; 3 Pages.

Paiva, et al. ; Using Standard Digital Extra-Oral Photography in Patient with Cleft Lip and Palate ; Int. J. Odontostomat., 13(3) ; pp. 345-349 ; 2019 ; 5 Pages.

Khoo, et al. ; A comparison between a photographic shade analysis system and conventional visual shade matching method ; Iowa Research Online ; Summer 2015 ; 141 Pages.

Hu, et al. ; New Algorithms in Shade Matching ; Republished with permission, Journal of Cosmetic Dentistry ; 2016 ; 11 pages.

Ahmad, "Standardization for Dental Photography Part 2", Journal of Cosmetic Dentistry vol. 36 Issue 3, pp. 44-63, 2020 (Year: 2020).

* cited by examiner

ADJUSTABLE DENTAL IMAGING DEVICE

CROSS-REFERENCE TO RELATED APPLICATIONS

The present application is a Continuation of U.S. application Ser. No. 18/766,721, now allowed, having a filing date of Jul. 9, 2024, which is a Continuation of U.S. application Ser. No. 18/623,386, now U.S. Pat. No. 12,059, 231, having a filing date of Apr. 1, 2024 which is a Continuation of U.S. application Ser. No. 17/319,771, now U.S. Pat. No. 11,980,445, having a filing date of May 13, 2021.

BACKGROUND

Field of the Invention

The present disclosure relates to an imaging device used in the dentistry, facial imaging and, more particularly relates, to a dental and facial imaging device and a method of assembling the dental and facial imaging device.

Discussion of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

With the advent of digital technology, imaging has become easier and more readily accessible. Particularly, application of digital imaging in dentistry, besides other medical fields, has gained importance over several years. For example, standardization and high-quality digital imaging are considered as fundamentals to assist in planning of a surgical procedure, to explain a treatment plan to a patient, to form a part of clinical diagnosis documentation, to pursue clinical investigations, and to assist in medico-legal cases. As such, standization of dental and facial images plays a key role in achieving quality images of patient's dental profile.

Known devices for dental and facial imaging includes large imaging devices which add to the cost of a corresponding imaging system and includes multiple components for adjusting position of patient's head which renders imaging process complex. As such, there exists a need for a dental and facial imaging device which is portable and easy to operate.

SUMMARY

According to one aspect of the present disclosure, a dental and facial imaging device is disclosed. The dental and facial imaging device includes an adjustable arm, an image sensor detachably mounted on a first end of the adjustable arm, and an adjustable patient positioning arm mounted on a second end of the adjustable arm. A distance between the adjustable patient positioning arm and the image sensor is adjustable based on an adjustable length of the adjustable arm. Further, the adjustable arm includes a position indicator scale having a plurality of notches utilized for calibrating the distance between the adjustable patient positioning arm and the image sensor. The adjustable patient positioning arm comprises a plurality of attachment devices including a detachable patient teeth supporting device and a detachable patient chin rest. The plurality of attachment devices on the adjustable patient positioning arm are positioned at a fixed coordinate reference relative to the image sensor to capture an image of a patient's teeth. The fixed coordinate reference corresponds to co-ordinates of a plurality of anatomical planes associated with the plurality of attachment devices relative to the image sensor.

In some embodiments, the plurality of attachment devices further includes a detachable patient head rest, and the plurality of attachment devices are configured to rotate along a horizontal axis corresponding with the plurality of attachment devices.

In some embodiments, the detachable patient head rest is positioned at a first end of the adjustable patient positioning arm, the detachable patient chin rest is positioned at a second end of the adjustable patient positioning arm, and the detachable patient teeth supporting device is positioned in between the detachable patient head rest and the detachable patient chin rest.

In some embodiments, a distance between the detachable patient head rest and the detachable patient teeth supporting device is adjustable based on the adjustable length of the adjustable patient positioning arm.

In some embodiments, a distance between the detachable patient chin rest and the detachable patient teeth supporting device is adjustable based on the adjustable length of the adjustable patient positioning arm.

In some embodiments, the detachable patient head rest is a head band to support a patient's head.

In some embodiments, a detachable patient head rest frame is attached to the second end of the adjustable arm and the detachable patient head rest frame is configured to support the detachable patient head rest.

In some embodiments, the adjustable patient positioning arm is in an upright position.

In some embodiments, wherein the plurality of anatomical planes includes an axial plane, a sagittal plane, and a coronal plane.

In some embodiments, the image sensor is a digital camera and the plurality of attachment devices are configured to move along a vertical axis corresponding with the plurality of attachment devices.

According to yet another aspect of the present disclosure, a method of manufacturing a dental and facial imaging device is disclosed. The method includes mounting an image sensor detachably on a first end of an adjustable arm and mounting an adjustable patient positioning arm on a second end of the adjustable arm. A distance between the adjustable patient positioning arm and the image sensor is adjustable based on an adjustable length of the adjustable arm. The adjustable arm includes a position indicator scale having a plurality of notches utilized for calibrating the distance between the adjustable patient positioning arm and the image sensor. The adjustable patient positioning arm comprises a plurality of attachment devices including a detachable patient teeth supporting device and a detachable patient chin rest. The plurality of attachment devices on the adjustable patient positioning arm are positioned at a fixed coordinate reference relative to the image sensor to capture an image of a patient's teeth. The fixed coordinate reference corresponds to co-ordinates of a plurality of anatomical planes associated with the plurality of attachment devices relative to the image sensor.

In some embodiments, the attachment device includes an adhesive device, and the plurality of attachment devices are configured to rotate along a horizontal axis corresponding with the plurality of attachment devices.

In some embodiments, the detachable patient head rest is positioned at a first end of the adjustable patient positioning arm, the detachable patient chin rest is positioned at a second end of the adjustable patient positioning arm, and the detachable patient teeth supporting device is positioned in between the detachable patient head rest and the detachable patient chin rest.

In some embodiments, a distance between the detachable patient head rest and the detachable patient teeth supporting device is adjustable based on the adjustable length of the adjustable patient positioning arm.

In some embodiments, a distance between the detachable patient chin rest and the detachable patient teeth supporting device is adjustable based on the adjustable length of the adjustable patient positioning arm.

In some embodiments, the detachable patient head rest is head band to support a patient's head.

In some embodiments, a detachable patient head rest frame is attached to the second end of the adjustable arm and the detachable patient head rest frame is configured to support a detachable patient head rest.

In some embodiments, the adjustable patient positioning arm is in an upright position.

In some embodiments, the plurality of anatomical planes includes an axial plane, a sagittal plane and a coronal plane.

In some embodiments, the image sensor is a digital camera and the plurality of attachment devices are configured to move along a vertical axis corresponding with the plurality of attachment devices.

These and other aspects and features of non-limiting embodiments of the present disclosure will become apparent to those skilled in the art upon review of the following description of specific non-limiting embodiments of the disclosure in conjunction with the accompanying drawings.

BRIEF DESCRIPTION OF THE DRAWINGS

A better understanding of embodiments of the present disclosure (including alternatives and/or variations thereof) may be obtained with reference to the detailed description of the embodiments along with the following drawings, in which.

DETAILED DESCRIPTION

Figure 1A:
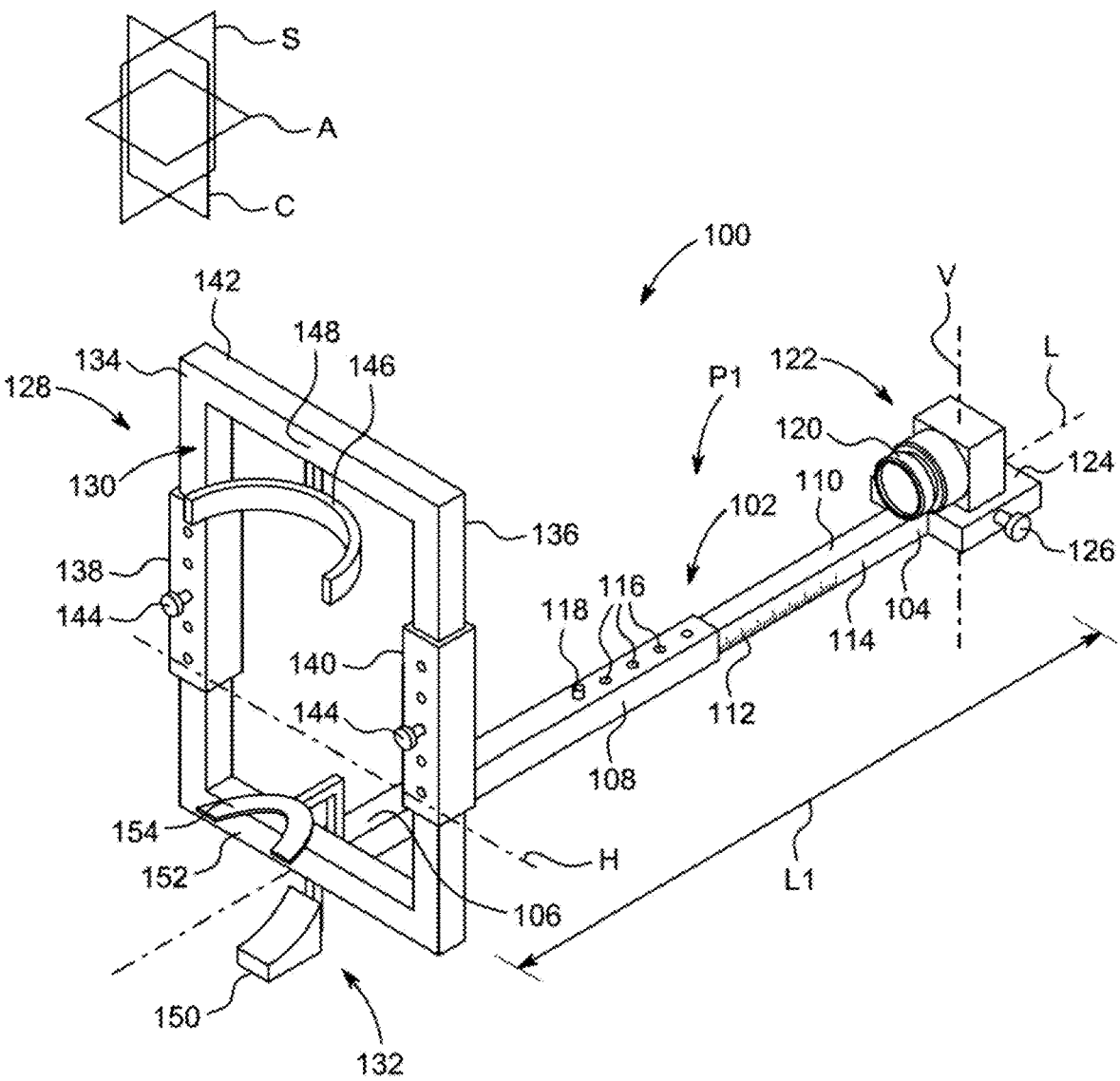
FIG. 1A illustrates a perspective view of a dental and facial imaging device in a first position, according to an embodiment of the present disclosure.

Reference will now be made in detail to specific embodiments or features, examples of which are illustrated in the accompanying drawings. Wherever possible, corresponding or similar reference numbers will be used throughout the drawings to refer to the same or corresponding parts. Moreover, references to various elements described herein, are made collectively or individually when there may be more than one element of the same type. However, such references are merely exemplary in nature. It may be noted that any reference to elements in the singular may also be construed to relate to the plural and vice-versa without limiting the scope of the disclosure to the exact number or type of such elements unless set forth explicitly in the appended claims.

In the drawings, like reference numerals designate identical or corresponding parts throughout the several views. Further, as used herein, the words "a," "an" and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values there between.

Aspects of the present disclosure are directed to a dental and facial imaging device that eases a process of dental and facial imaging by stably positioning patient's head and adjusting distance between an imaging device and the patient's head with aid of simple construction.

Figure 1B:
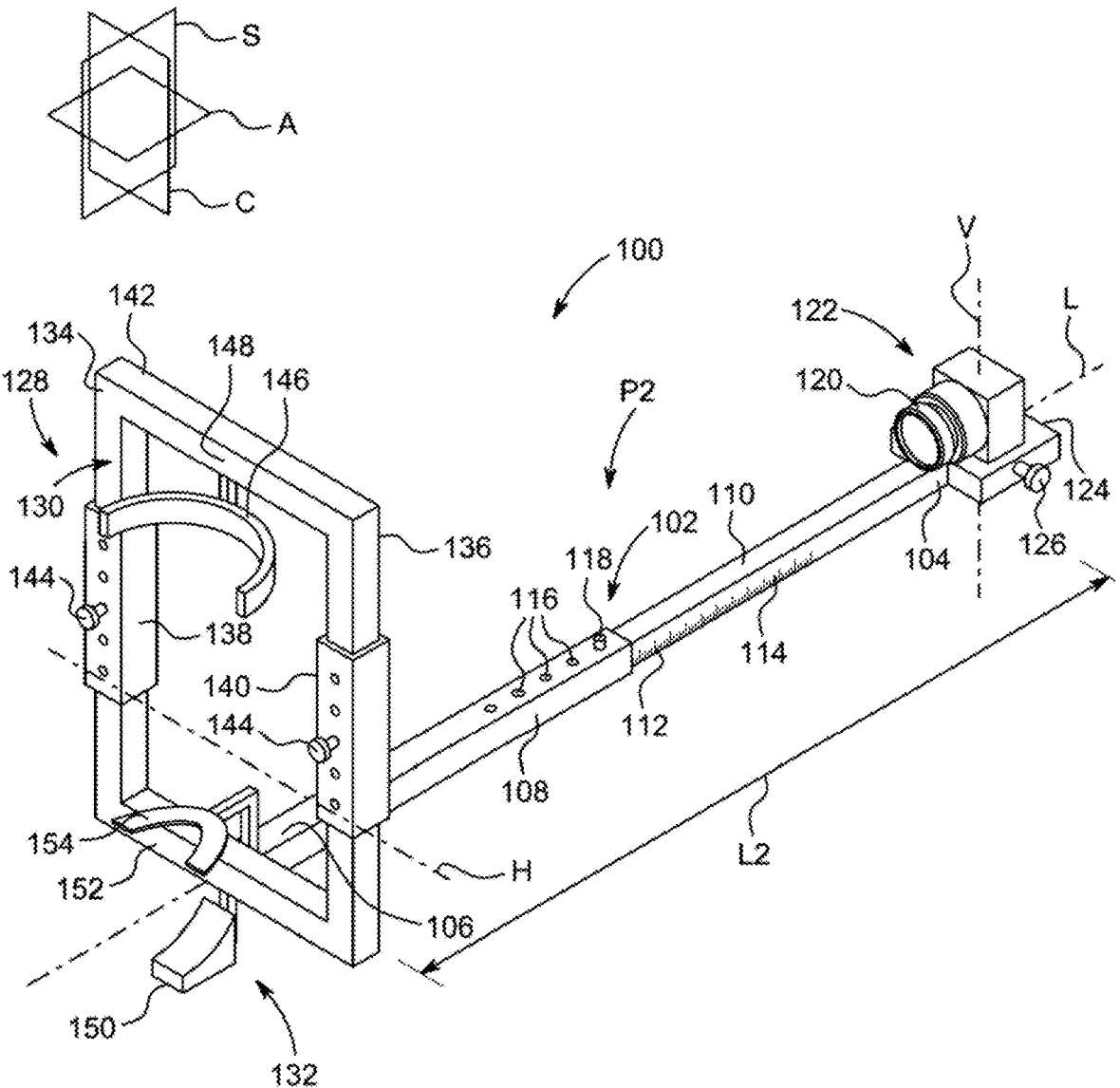
FIG. 1B illustrates a perspective view of the dental and facial imaging device in a second position, according to an embodiment of the present disclosure.

FIG. 1A illustrates a perspective view of a dental and facial imaging device 100 (hereinafter referred to as "the device 100") in a first position "P1" and FIG. 1B illustrates the perspective view of the device 100 in a second position "P2". The device 100 includes an adjustable arm 102 having a first end 104 and a second end 106. In an embodiment, the adjustable arm 102 includes a telescopic arrangement to allow length adjustment thereof. The telescopic arrangement includes a stationary member 108 and a movable member 110 slidably disposed within the stationary member 108. In an example, the movable member 110 is configured to move in a direction along a longitudinal axis "L" of the adjustable arm 102 with respect to the stationary member 108. The stationary member 108 may be detachably fixed to a table using a clamp, such that a sliding movement of the movable member 110 with respect to the stationary member 108 may be manually handled.

Further, the adjustable arm 102 includes a position indicator scale 112. In an embodiment, the position indicator scale 112 may be provided on a side surface 114 of the movable member 110. For example, the position indicator scale 112 may include multiple incremental gradation markings on the side surface 114 to indicate a length by which the movable member 110 is moved with respect to the stationary member 108. However, it will be apparent to a person skilled in the art that digital meters and other devices capable of indicating the length of movement may be employed in the adjustable arm 102.

The position indicator scale 112 includes a plurality of notches 116 that are sequentially positioned in a straight line and utilized for calibrating the length of movement of the movable member 110 with respect to the stationary member 108. In embodiments, the stationary member 108 defines notches 116 and the movable member 110 includes a button 118 configured to engage with each of the notches 116. The notches 116 are illustrated as holes in FIG. 1A and FIG. 1B. In one example, the button 118 may be embodied as a spring loaded pin and is fixed on the movable member 110, where pressing of the button 118 into the notch 116 allows disengagement of the movable member 110 from the stationary member 108 and allows sliding movement of the movable member 110 along with the button 118 pressed into the notches 116. When the button 118 reaches the next sequential notch 116 on the stationary member 108, the button 118 is aligned with the notch 116, and causes release of the button 118 which allows the button 118 to extend through the notch 116 to lock the movable member 110 with the stationary member 108. As such, the movable member 110 may be locked at any desired position (also referred to as "adjustable length" in the present disclosure) by locking the button 118 with one of the notches 116. FIG. 1B illustrates the device 100 in the second position "P2", where the button 118 is engaged with the notch 116 located at an extreme end of the stationary member 108, indicating a maximum adjustable length for sliding the movable member 110 with respect to the stationary member 108.

Therefore, the plurality of notches 116 and the button 118 together aid in calibrating the length of movement of the movable member 110 with respect to the stationary member 108. Particularly, the position indicator scale 112 helps a user of the device 100 to move the movable member 110 by a desired length with respect to the stationary member 108 as shown in FIG. 1B. Although the telescopic arrangement is described herein for the purpose of adjusting the adjustable arm 102 to the desired length, multiple other embodiments may be apparent to the person skilled in the art. For example, the button 118 may be replaced with a knob (not shown) and the movable member 110 may define a set of holes, where each hole is configured to engage with the knob for locking the movable member 110 at the desired length. In another example, sliding arrangement with track and slider may be used to achieve the adjustable configuration of the adjustable arm 102.

The device 100 further includes an image sensor 120 detachably mounted to the first end 104 of the adjustable arm 102. As used herein, the term "image sensor 120" refers to a sensor that detects and conveys information to produce an image. In an embodiment, the image sensor 120 may be implemented in a camera device 122. In an example, the camera device 122 may be one of a digital single lens reflex (DSLR) camera, a smartphone camera, a compact camera, a mirrorless camera, a 360-degree camera, a film camera, a bridge camera, an instant camera, a medium format camera, a point and shoot camera or any other camera known in the person skilled in the art for the purpose of dental and facial imaging, preferably a digital camera. In an embodiment, the camera device 122 may be mounted on an adjustable base 124 detachably coupled to the first end 104 of the adjustable arm 102. In an example, the adjustable base 124 may be configured to secure the camera device 122. The adjustable base 124 may be 3D printed with suitable rigid material and includes a knob 126 configured to adjust position of the camera device 122 along a vertical axis "V".

The device 100 further includes an adjustable patient positioning arm 128 mounted in an upright position on the second end 106 of the adjustable arm 102. The adjustable patient positioning arm 128 includes a frame 130 provided as a rectangular structure, and a plurality of attachment devices 132 adjustably coupled to the frame 130. As used herein, the term "adjustably coupled" refers to provision for adjusting each of the plurality of attachment devices 132 along the vertical axis "V", a horizontal axis "H", or to any desired orientation with respect to the frame 130. In an embodiment, each of a left vertical arm 134 and a right vertical arm 136 of the frame 130 includes another telescopic arrangement to allow configuring the frame 130 to various lengths along the vertical axis "V". For example, the telescopic arrangement of the frame 130 includes a first slider 138 provided on the left vertical arm 134 and a second slider 140 provided on the right vertical arm 136. Independent manual adjustment of the first slider 138 and the second slider 140 allows an adjustable portion 142 of the frame 130 to be lifted along the vertical axis "V" and secured at desired extended length with aids of knobs 144.

The plurality of attachment devices 132 includes a detachable patient head rest 146 embodied as an arcuate member configured to conform to the head of a patient. The detachable patient head rest 146 is positioned at a first end 148 of the adjustable patient positioning arm 128. As such, the frame 130 is configured to support the detachable patient head rest 146. In an embodiment, a curvature of the arcuate member may be changed based on the patient. For example, the curvature of the arcuate member may differ for an adult patient and a child. In some embodiments, the detachable patient head rest 146 is a head band to support the head of the patient and retain the patient's head still.

The plurality of attachment devices 132 further includes a detachable patient chin rest 150 positioned at a second end 152 of the adjustable patient positioning arm 128, and a detachable patient teeth supporting device 154 positioned in between the detachable patient head rest 146 and the detachable patient chin rest 150. In an embodiment, the detachable patient teeth supporting device 154 may include a removable non-toxic rubber material to allow the patient to rest the teeth thereon during dental and facial imaging. In another embodiment, the plurality of attachment devices 132 may include an adhesive device, for example a double-sided tape, a super glue, an epoxy resin, a fabric adhesive or any adhesive known in the art, particularly on an inner surface of each of the detachable patient head rest 146 and the detachable patient chin rest 150, to receive a foam layer for providing comfort to the patient. The plurality of attachment devices 132 are configured to rotate along the horizontal axis "H" corresponding with the plurality of attachment devices 132. Such provision for rotation the plurality of attachment devices 132 along the horizontal axis "H" allows patient's face to be fixed at a desired orientation with respect to the frame 130. In another embodiment, each of the plurality of attachment devices 132 is configured to move along the vertical axis "V" corresponding with the plurality of attachment devices 132.

Owing to the presence of the adjustable arm 102, the distance between the adjustable patient positioning arm 128 and the image sensor 120 is adjustable based on the adjustable length of the adjustable arm 102. As used herein, the term "adjustable length" refers to the provision of moving the movable member 110 with respect to the stationary member 108 of the adjustable arm 102 to configure the adjustable arm 102 to the desired length. As such, the adjustable arm 102 and the position indicator scale 112 are together utilized for calibrating the distance between the adjustable patient positioning arm 128 and the image sensor 120.

As seen in FIG. 1A and FIG. 1B, the distance between the adjustable patient positioning arm 128 and the image sensor 120 is increased from "L1" to "L2". As such, the image sensor 120, particularly the camera device 122, may be located at a desired distance from the adjustable patient positioning arm 128. Such provision overcomes requirement of multiple focal lenses to be implemented in the camera device 122. In an embodiment, a distance between the detachable patient head rest 146 and the detachable patient teeth supporting device 154 is adjustable based on the adjustable length of the adjustable patient positioning arm 128. In another embodiment, a distance between the detachable patient chin rest 150 and the detachable patient teeth supporting device 154 is adjustable based on the adjustable length of the adjustable patient positioning arm 128.

Further, the plurality of attachment devices 132 are positioned at a fixed coordinate reference relative to the image sensor 120 to capture an image of patient's teeth. The fixed coordinate reference corresponds to co-ordinates of a plurality of anatomical planes associated with the plurality of attachment devices 132 relative to the image sensor 120. The plurality of anatomical planes includes an axial plane "A", a sagittal plane "S" and a coronal plane "C" as shown in FIG. 1A and FIG. 1B. The axial plane "A" bisects the patient's face into top portion and bottom portion, the sagittal plane "S" bisects the patient's face into left portion and right portion, and the coronal plane "C" bisects the patient's face into front portion and rear portion. In order to achieve a desired dental and facial image, the patient's face needs to be positioned appropriately with respect to the axial plane "A", the sagittal plane "S" and the coronal plane "C". Resulting co-ordinates points corresponding to the orientation of the patient's face may be understood as the "fixed coordinate" as used herein. In an embodiment, the fixed coordinate for each patient may be measured and be stored in a computing system (not system) disposed in communication with the device 100. In an example, upon positioning the patient's head at required orientation to achieve better capturing of the patient's teeth, the computing system may be configured to automatically fetch the data related to the fixed coordinates from the device 100. Data of multiple sets of fixed coordinates corresponding to various orientation of the patient's face may also be stored in the computing system. Such data may be used to easily position the adjustable patient positioning arm 128, either manually or automatically, during subsequent dental and facial imaging sessions of the patient. Similarly, data of the fixed coordinates of multiple patients may be stored. In some embodiment, an angular position indicator (not shown) may be used to measure an angular orientation of the patient's face, and such angular position data may also be stored along with the fixed coordinates.

Figure 1C:
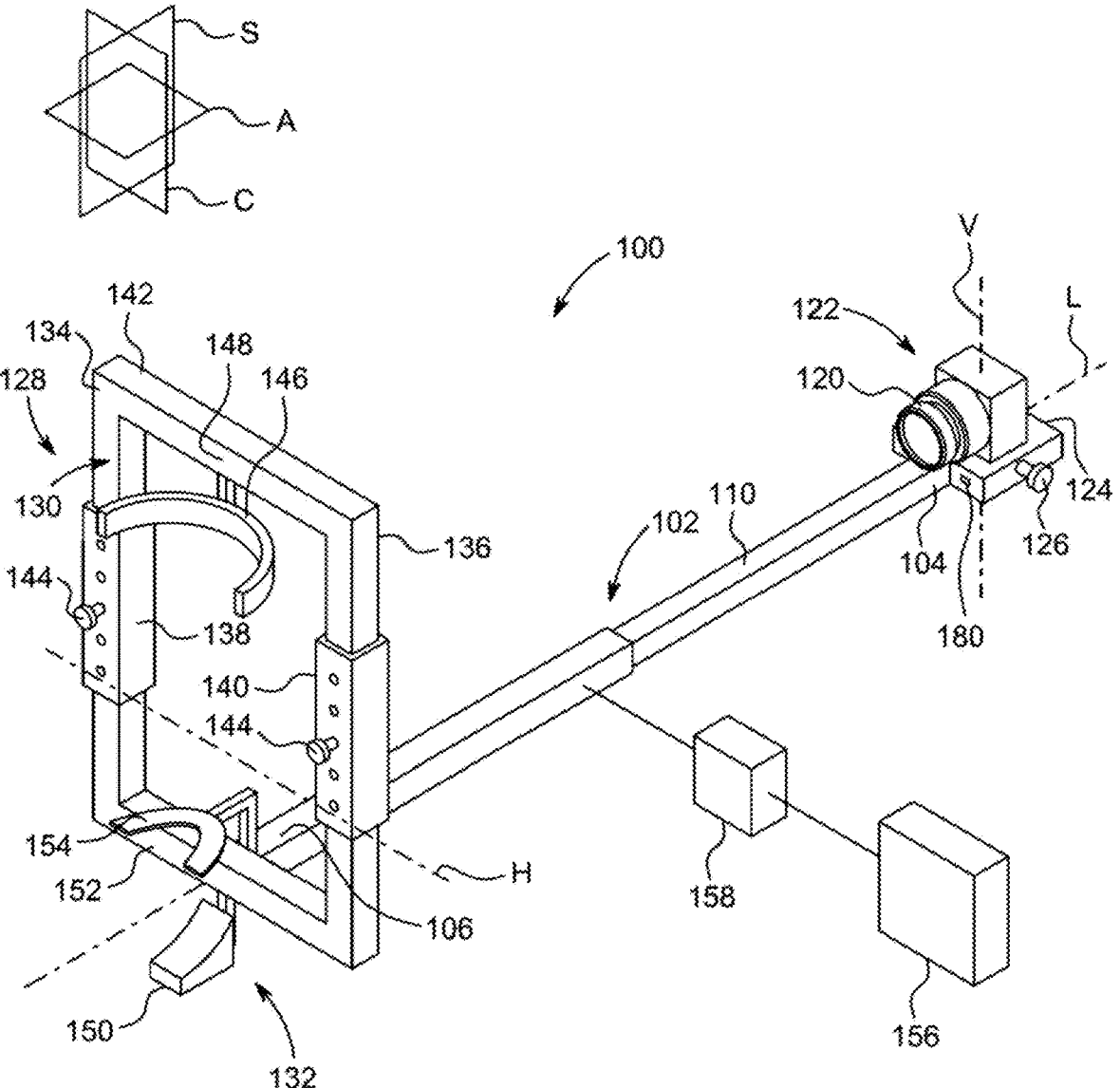
FIG. 1C illustrates a perspective view of the dental and facial imaging device coupled to an arm adjusting system, according to an embodiment of the present disclosure.

FIG. 1C illustrates an arm adjusting system 156 coupled to the adjustable arm 102, according to an embodiment of the present disclosure. The arm adjusting system 156 (hereinafter referred to as "the system 156") is configured to adjust the distance between the adjustable patient positioning arm 128 and the camera device 122 by causing the relative movement between the stationary member 108 and the movable member 110 along the longitudinal axis "L". To aid such adjustment, the device 100 includes a motor 158 coupled to the adjustable arm 102. In an embodiment, the relative movement between the stationary member 108 and the movable member 110 may be achieved through a linear actuator, for example, a gear arrangement, such as a rack and a pinion arrangement, instead of the notches 116 and the button 118. For example, the rack and pinion arrangement may be coupled between the stationary member 108 and the movable member 110, and the motor 158 may be coupled to the pinion to aid the relative movement. As such, rotation of a shaft (not shown) of the motor 158 causes the pinion to rotate, thereby resulting in a linear travel of the rack and desired adjustment of the adjustable arm 102.

Figure 1D:
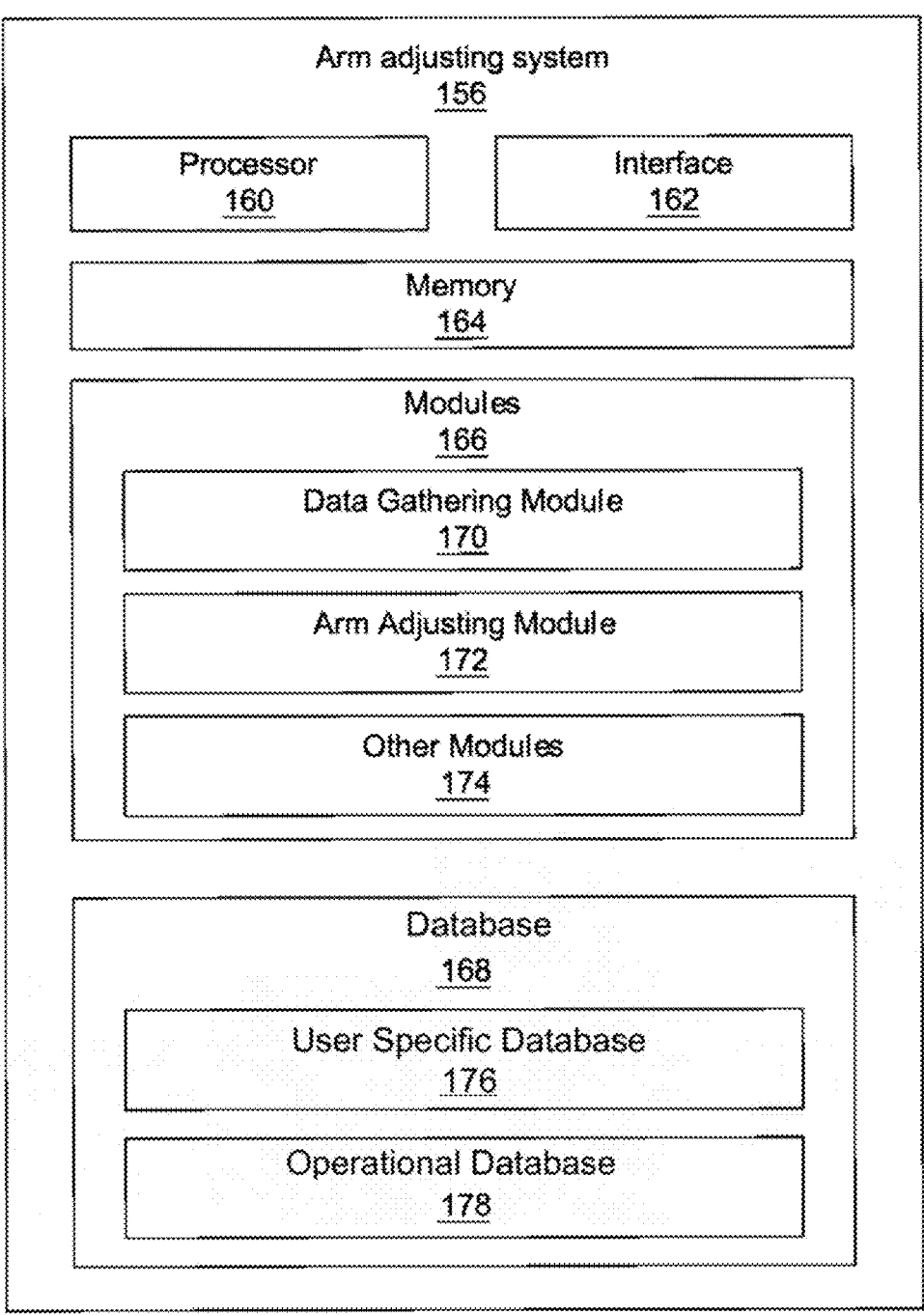
FIG. 1D illustrates a block diagram of the arm adjusting system of FIG. 1C, according to an embodiment of the present disclosure.

FIG. 1D illustrates exemplary components of the system 156. In an embodiment, the system 156 includes processor (s) 160, interface(s) 162 and a memory 164. The processor (s) 160 may be embodied as a single processing unit or a number of processing units, all of which could include multiple computing units. The processor(s) 160 may be implemented as one or more microprocessor, microcomputers, digital signal processors, central processing units, state machines, logic circuitries, and/or any devices that manipulate signals based on operational instructions. Among other capabilities the processor(s) 160 are adapted to receive or fetch and execute computer-readable instructions stored in the memory 164.

Functions of the various elements shown in the FIG. 1D, including functional blocks labeled as "processor(s)", may be provided through use of dedicated hardware as well as hardware capable of executing software in association with appropriate software. Moreover, explicit use of the term "processor" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), non-volatile storage. Other hardware, conventional or custom, may also be included as known to the person skilled in the art.

The interface(s) 162 may include a variety of software and hardware interfaces, for example, interface for peripheral device(s), such as a keyboard, a mouse, a microphone, an external memory, a speaker, and a printer. Further, the interface(s) 162 may include one or more ports for connecting the system 156 with other computing devices, such as web servers, and external databases. The interface(s) 162 may facilitate multiple communications within a wide variety of protocols and networks, such as a network, including wired networks, e.g., LAN, cable, etc., and wireless networks, e.g., WLAN, cellular, satellite, and the like.

The memory 164 may be coupled to the processor 160 and may include any computer-readable medium known in the art including, for example, volatile memory, such as Static Random Access Memory (SRAM) and Dynamic Random Access Memory (DRAM), and/or non-volatile memory, such as Read Only Memory (ROM), Erasable Programmable ROMs (EPROMs), flash memories, hard disks.

The system 156 may also include module(s) 166 and a database 168. The modules 166 and the database 168 may be coupled to the processors 160. The modules 166 may include routines, programs, objects, components, data structures, etc., which perform tasks. The modules 166 may also be implemented as, signal processor(s), state machine(s), logic circuitries, and/or any other device or component that manipulate signals based on operational instructions. In another aspect of the present disclosure, the modules 166 may be computer-readable instructions which, when executed by a processor/processing unit, perform any of the described functionalities. The computer-readable instructions may be stored on an electronic memory device, hard disk, optical disk or other machine-readable storage medium or non-transitory medium. In one implementation, the computer-readable instructions can be also be downloaded to a storage medium via a network connection.

Without limitation, the module(s) 166 includes, for example, a data gathering module 170, an arm adjusting module 172, and other module(s) 174. The other module(s) 174 include programs that supplement applications or functions performed by the system 156. The database 168 serves, amongst other functions, as a repository for storing data obtained and processed by one or more module(s) 166. The database 168 includes, for example, user specific data 176 and an operational database 178. The operational database 178 includes data generated as a result of the execution of one or more modules in the other module(s) 174.

The system 156 will be described in conjunction with FIG. 1C. According to an aspect of the present disclosure, the system 156 may be physically coupled to the device 100 or may be integrally disposed as a component of the device 100. In an embodiment, the data gathering module 170 may be coupled to a user interface (not shown), for example, a keypad and a screen to display inputs received through the keypad, or a touch screen configured to receive inputs from the user, or a joystick. A desired distance between the adjustable patient positioning arm 128 and the camera device 122 may be input using the user interface. The desired distance may be increased or decreased in small graduations by utilizing "increase" or "decrease" keypad buttons or touch buttons (not shown in drawings) provided in the user interface. In case of joystick, forward and backward movement of the joystick may correspond to increase or decrease in the desired distance between the adjustable patient positioning arm 128 and the camera device 122. In some implementations, the joystick may be supported by the keypad or touchscreen to receive inputs for small adjustments to the desired distance, such inputs received through the user interface may be stored in the user specific data 176.

In an implementation, upon setting the desired distance between the adjustable patient positioning arm 128 and the camera device 122, the data gathering module 170 may request the user to confirm the setting. Upon confirmation, the data pertaining to the setting may be stored in the user specific data 176. Particularly, the distance "L1" at the first position "P1" of the device 100 and the distance "L2" at the second position "P2" of the device 100 may be stored in the user specific data 176. In some implementations, as will be apparent to the person skilled in the art, the user interface may also be configured to receive personalized data relating to name of the patient, age of patient, and the like. As such, a profile of the patient may be created, including date and time of profile creation, and the distance setting data may be tagged with the profile and may be stored in the user specific data 176. With such arrangement, the required distance between the adjustable patient positioning arm 128 and the camera device 122 may be readily gathered for a patient.

Based on the inputs received through the user interface, or the data gathered from the user specific data 176, the arm adjusting module 172 may actuate the motor 158 to cause relative movement between the stationary member 108 and the movable member 110 of the adjustable arm 102. The relative movements between the stationary member 108 and the movable member 110 of the adjustable arm 102 thereby adjust the adjustable arm 102 to achieve the desired distance between the adjustable patient positioning arm 128 and the camera device 122. In an embodiment, the motor 158 may be a stepper motor and a magnitude of electric current supplied to the motor 158 may be regulated by the arm adjusting module 172.

In order to determine the desired distance between the adjustable patient positioning arm 128 and the camera device 122 during operation of the motor 158, the device 100 may include a proximity sensor 180. In an embodiment, the proximity sensor 180 may be coupled to the adjustable base 124 to sense the desired distance between the adjustable patient positioning arm 128 and the camera device 122 during the relative movement between the stationary member 108 and the movable member 110 of the adjustable arm 102. The proximity sensor 180 may be embodied as one of, but not limited to, a laser based sensor, infrared based sensor, or ultrasonic wave sensor. The system 156 may be communicably coupled to the proximity sensor 180, such that the arm adjusting module 172 is configured to receive inputs from the proximity sensor 180. The arm adjusting module 172 may be configured to actuate the motor 158 until the desired distance received as inputs from the user interface is equal to the distance sensed by the proximity sensor 180. As such, the system 156 may allow adjustment of the adjustable arm 102.

Figure 1E:
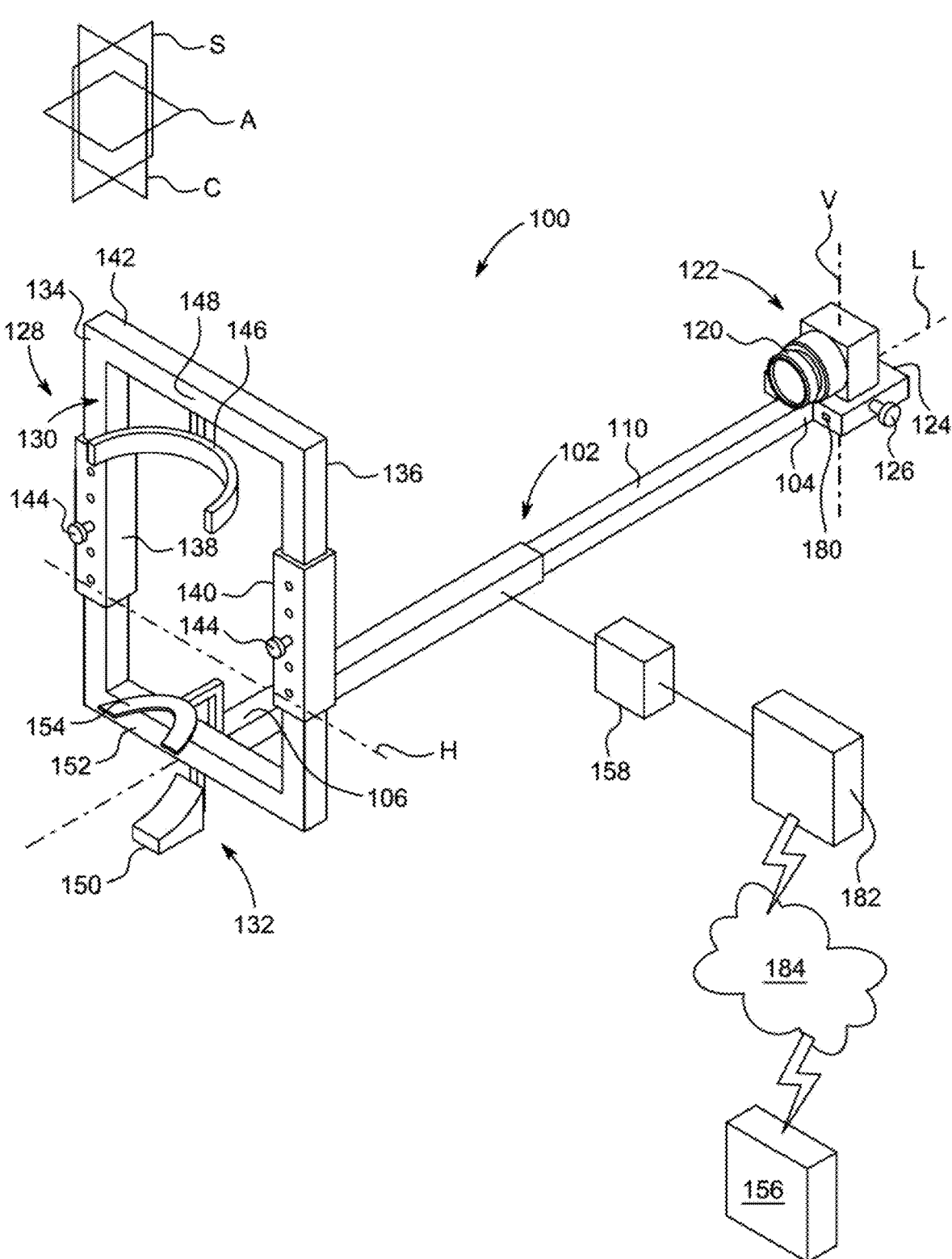
FIG. 1E illustrates a perspective view of the dental and facial imaging device coupled to the arm adjusting system, according to another embodiment of the present disclosure.

According to another aspect of the present disclosure, the system 156 may be coupled to the device 100 via a wireless communication. For example, the system 156 may be implemented in a computing device, such as, but not limited to, a laptop computer, a desktop computer, hand-held devices, portable computers, tablet computers, mobile phones, PDAs, Smartphones, and the like. In such arrangement, the system 156 may establish communication with the motor 158 and the proximity sensor 180 via a network 184. For example, the motor 158 and the proximity sensor 180 may be coupled to a local controller 182 of the device 100 and the local controller 182 may be configured to establish wireless communication with the system 156 via the network 184, as illustrated in FIG. 1E. It will be apparent to the person skilled in the art that the local controller 182 may be equipped with wireless communication modules for the purpose of establishing communication with the system 156 and may be embodied similar to the processor 160 of the system 156. As such, the arm adjusting module 172 may be configured to communicate the user inputs to the local controller 182 to adjust the adjustable arm 102 to the desired distance. Based on the receipt of the user inputs, the local controller 182 may be configured to actuate the motor 158 to cause the relative movement between the stationary member 108 and the movable member 110 to achieve the desired distance between the adjustable patient positioning arm 128 and the camera device 122.

Figure 2A:
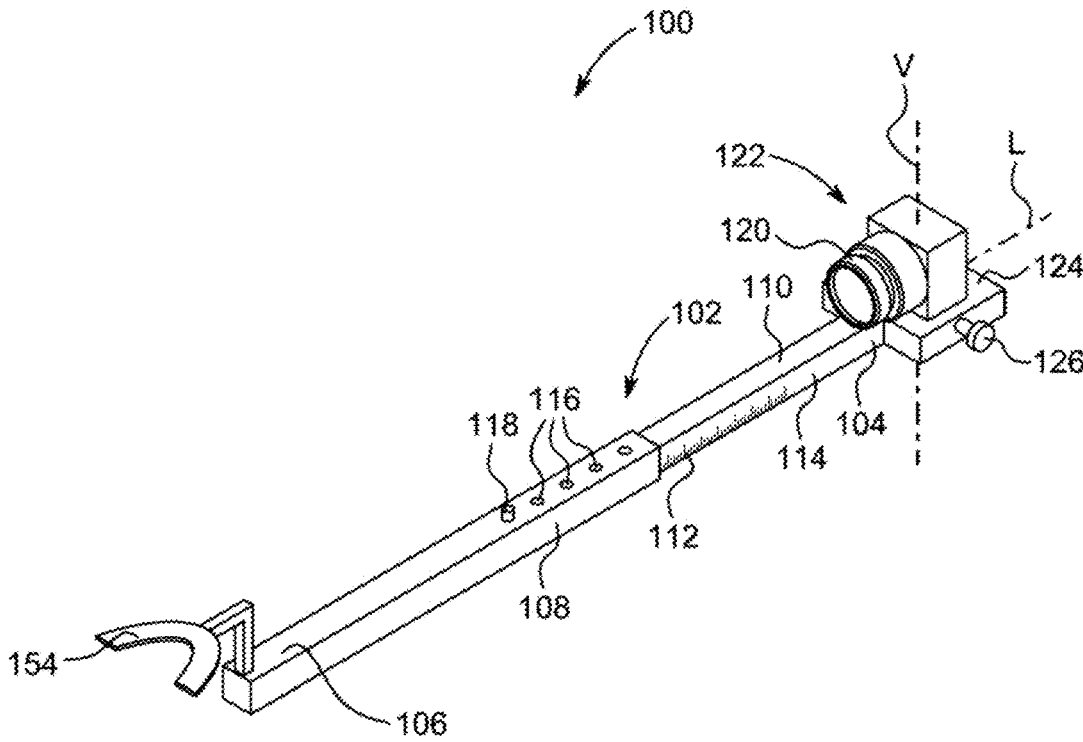
FIGS. 2A and 2B illustrates optional configurations of the dental and facial imaging device, according to various embodiment of the present disclosure.
Figure 2B:
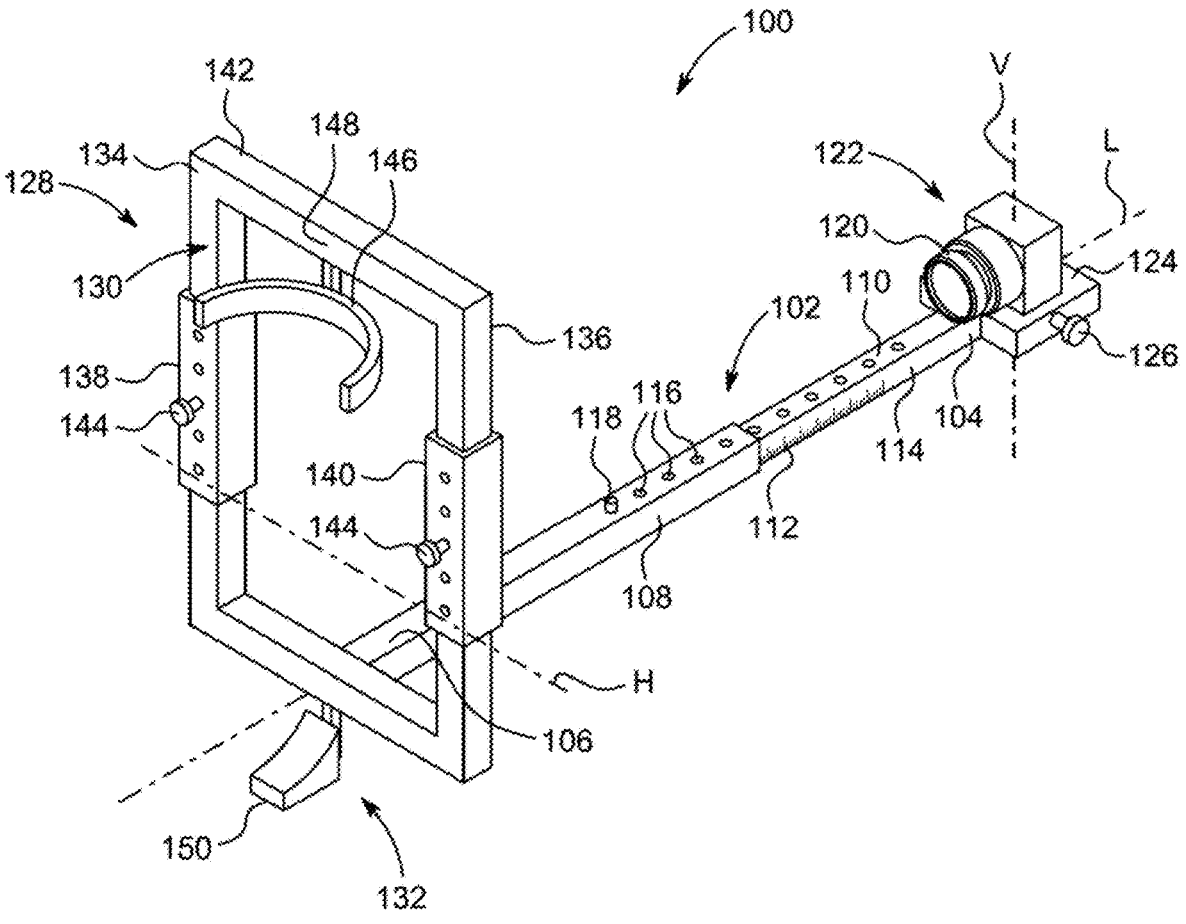

FIGS. 2A and 2B illustrates an embodiment of the device 100. As shown in FIG. 2A, the device 100 may include only the detachable patient teeth supporting device 154. With the help of the knob 126 provided on the adjustable base 124, the camera device 122 may be adjusted to a desired height along the vertical axis "V" to obtain desired dental and facial images of the patient. In another embodiment, the device 100 may include only the frame 130, the detachable patient head rest 146, and the detachable patient chin rest 150. In such embodiments, the provision of the adjustable arm 102 allows varying the distance between the patient's teeth and the camera device 122, thereby obtaining dental and facial images of required focus and magnification.

Figure 3:
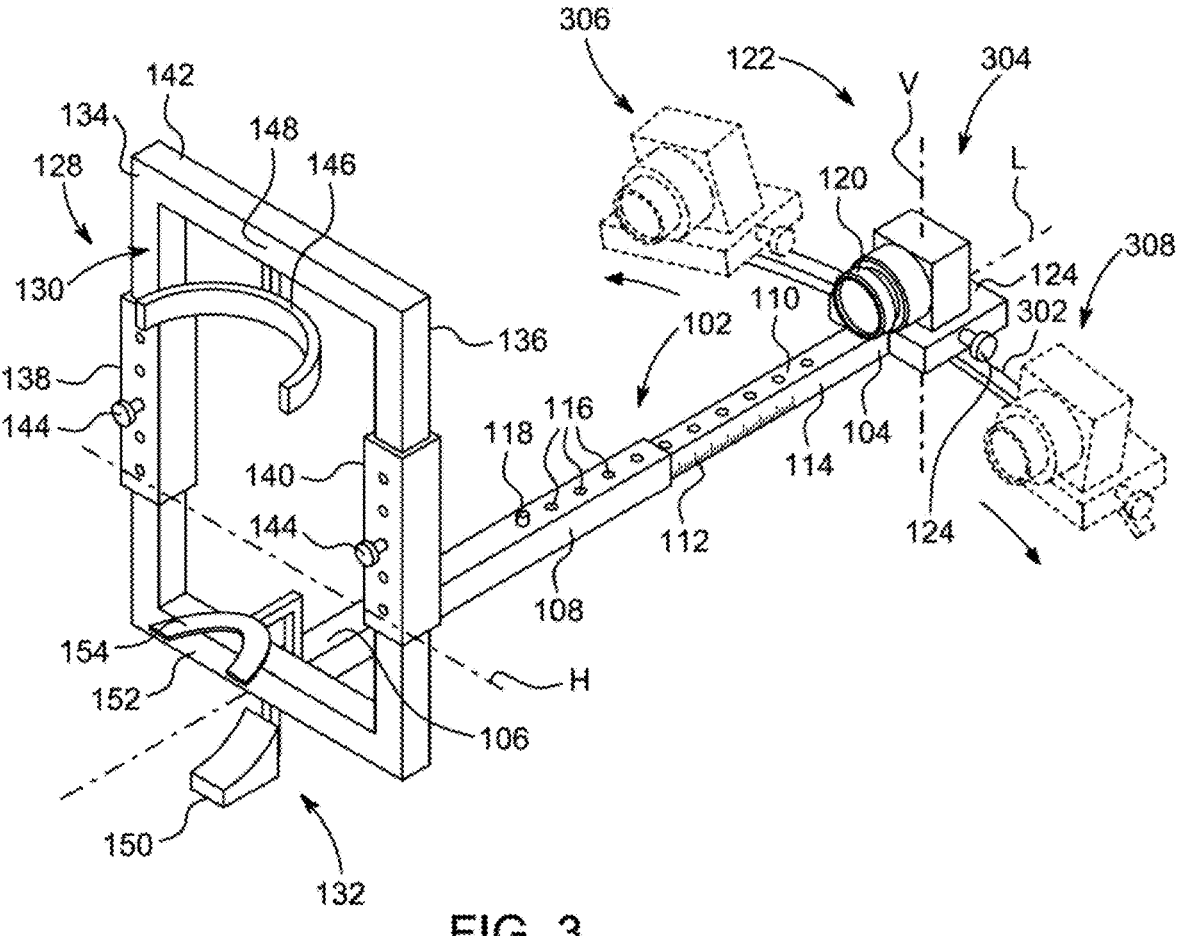
FIG. 3 illustrates the dental and facial imaging device, according to another embodiment of the present disclosure.

FIG. 3 illustrates the device 100, according to another embodiment of the present disclosure. The device 100 may further include a track 302 extending through the adjustable base 124. With the help of the track 302, the adjustable base 124 may be allowed to move sideways with respect to the vertical axis "V". In an embodiment, the track 302 may extend in an arcuate manner as shown in FIG. 3. As such, the camera device 122, particularly the image sensor 120, is allowed to radially move along the track 302 with respect to the adjustable patient positioning arm 128.

A neutral position 304 of the image sensor 120 is illustrated in FIG. 3 and such neutral position 304 allows image capture of a front portion of the teeth of the patient. The camera device 122 may be moved along the track 302 to a first radial position 306 to capture images of the teeth present on one side of the front portion. Similarly, the camera device 122 may be moved along the track 302 to a second radial position 308 to capture images of the teeth present on other side of the front portion. All the images may be analyzed and collated by an image analyzer (not shown) to arrive at desired dental and facial images.

Figure 4:
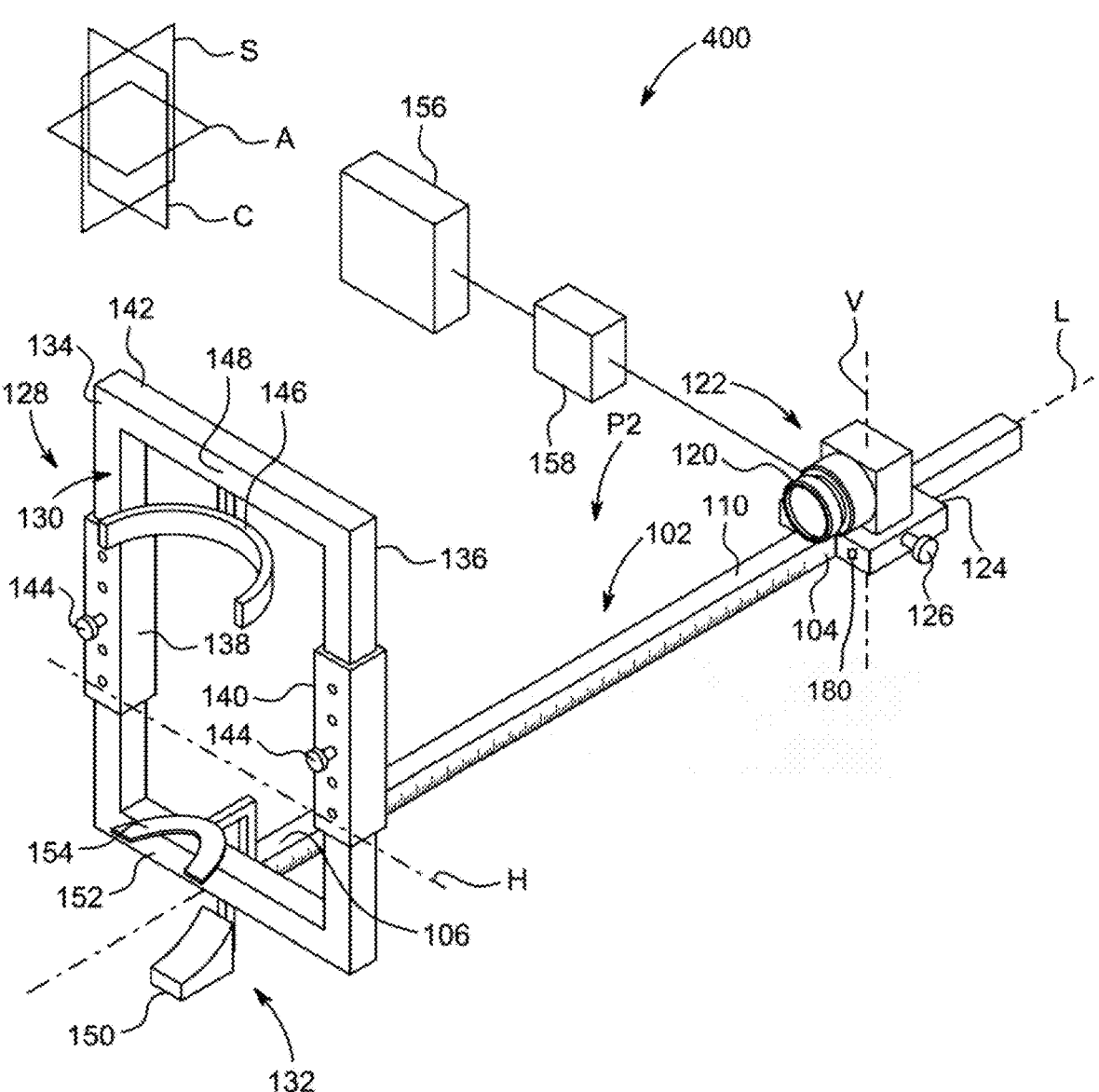
FIG. 4 illustrates a perspective view of the dental and facial imaging device coupled to the arm adjusting system without a stationary member, according to an embodiment of the present disclosure.

FIG. 4 illustrates a dental and facial imaging device 400 (alternatively referred to as "the device 400"). FIG. 4 will be described with reference to FIG. 1C, FIG. 1D, and FIG. 1E. In an embodiment, the device 400 does not include the stationary member 108, and hence the movable member 110 extends between the first end 104 and the second end 106 of the adjustable arm 102. In such arrangement, the distance between the adjustable patient positioning arm 128 and the camera device 122 may be adjusted by moving the camera device 122 relative to the adjustable patient positioning arm 128. In an embodiment, the adjustable base 124 may be movably disposed on the movable member 110. The linear actuator may be provided between abutting surfaces of the adjustable base 124 and the movable member 110. For example, the pinion gear may be rotatably coupled to the adjustable base 124 and the rack gear may be provided on the movable member 110 and may extend along the longitudinal axis "L" of the device 400. As such, rotation of the pinion gear results in movement of the adjustable base 124, and hence the camera device 122, relative to the adjustable patient positioning arm 128.

In an embodiment, the proximity sensor 180 may be coupled to the adjustable base 124 to sense the distance between the camera device 122 and the adjustable patient positioning arm 128. The system 156 may be operably coupled to the device 400 to adjust the distance between the camera device 122 and the adjustable patient positioning arm 128 based on the user inputs. Particularly, the arm adjusting module 172 may be configured to actuate the motor 158 based on the user inputs, where the actuation of the motor 158 causes rotation of the pinion gear in a respective direction to move the camera device 122 relative to the adjustable patient positioning arm 128.

In another embodiment, the system 156 may be located remote with respect to the device 400 and may be communicably coupled to the device 400 via the network 184. Specifically, the arm adjusting module 172 of the system 156 may be configured to communicate with the local controller 182 to actuate the motor 158.

In yet another embodiment, the proximity sensor 180 may be deployed within the camera device 122 and may be coupled to any component of the camera device 122 to sense the distance between the adjustable patient positioning arm 128 and the camera device 122.

Figure 5:
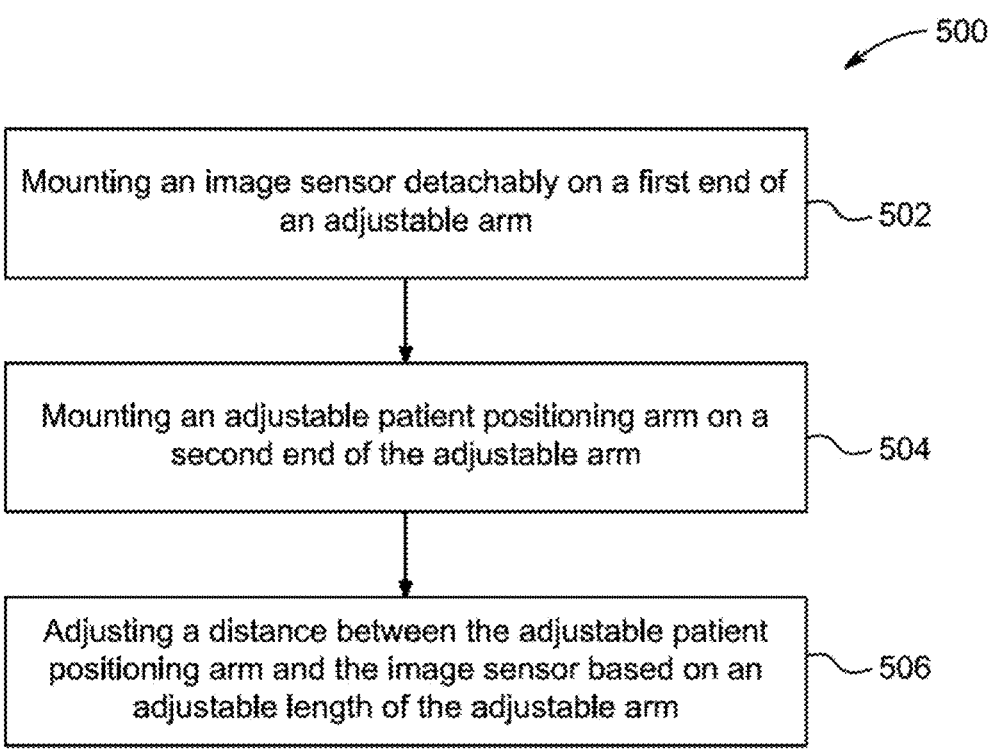
FIG. 5 illustrates a flowchart of a method of manufacturing the dental and facial imaging device, according to an embodiment of the present disclosure.

FIG. 5 illustrates a flowchart of a method 500 of manufacturing the device 100, according to an embodiment of the present disclosure. The method 500 is described in conjunction with FIG. 1A through FIG. 1E. Various steps of the method 500 are included through blocks in FIG. 5. One or more blocks may be combined or eliminated to arrive at the device 100 without departing from the scope of the present disclosure.

At step 502, the method 500 includes mounting the image sensor 120 detachably on the first end 104 of the adjustable arm 102. The method 500 further includes mounting the image sensor 120 on the adjustable base 124 and detachably mounting the adjustable base 124 on the first end 104 of the adjustable arm 102.

Ate step 504, the method 500 includes mounting the adjustable patient positioning arm 128 on the second end 106 of the adjustable arm 102.

At step 506, the method 500 includes adjusting the distance between the adjustable patient positioning arm 128 and the image sensor 120 based on the adjustable length of the adjustable arm 102. In an embodiment, the method 500 includes receiving inputs from the user pertaining to the desired distance between the adjustable patient positioning arm 128 and the camera device 122. Based on the received inputs, the method 500 includes actuating the motor 158, by the arm adjusting module 172, to cause movement of the movable member 110 with respect to the stationary member 108.

As described earlier, the adjustable arm 102 allows the camera device 122 to be positioned at the desired length from the patient's teeth, thereby allowing capture of multiple images of the patient's teeth corresponding to varied focal lengths and magnification. Additionally, the flexibility of the attachment devices 132 of the adjustable patient positioning arm 128 allows the patient's head to be positioned still at desired orientation, thereby achieving accuracy in dental and facial imaging, case documentation, and enhancing research efficiency. Due to the ease of handling and adjustment, the device 100 can be used by clinicians. The device 100 may be helpful in capturing identical images of the patient since the fixed coordinates for positioning of the patient head may be easily noted or stored. It will be apparent to the person skilled in the art that the use of the device 100 may be extended to dental clinics, portrait photography, research based on facial photography, ear nose and throat (ENT) and ophthalmology studies.

Numerous modifications and variations of the present disclosure will be apparent to the person skilled in the art in light of the above description. Position, shape, and size of components of the device 100 described herein are only for the purpose of illustration and should not be considered as limiting. It is therefore to be understood that within the scope of the appended claims, the invention may be practiced otherwise than as specifically described herein.

The invention claimed is:

1. An adjustable dental imaging device, comprising:
    a telescoping adjustable arm having a stationary member and a movable member slidably disposed within the stationary member, wherein the telescoping adjustable arm is configured to adjust an adjustable length of the telescoping adjustable arm by sliding the movable member within the stationary member;
    an image sensor detachably mounted on an adjustable base at a first end of the adjustable arm;
    an adjustable patient positioning arm directedly mounted on a second end of the adjustable arm, wherein a distance between the adjustable patient positioning arm and the image sensor in a first direction is adjustable based on the adjustable length of the telescoping adjustable arm in the first direction and wherein the telescoping adjustable arm includes a position indicator scale, the position indicator scale including a plurality of notches utilized for calibrating the distance in the first direction between the adjustable patient positioning arm and the image sensor;

an infrared sensor or an ultrasonic wave sensor coupled to the adjustable base and configured to sense a distance between the adjustable patient positioning arm and the image sensor;

the adjustable patient positioning arm comprising a plurality of attachment devices, wherein the plurality of attachment devices includes a detachable patient teeth supporting device, and a detachable patient chin rest; and the plurality of attachment devices on the adjustable patient positioning arm are positioned relative to the image sensor to capture an image of a patient's teeth, wherein the image sensor is adjustable in a vertical direction perpendicular to the first direction, and wherein the detachable patient teeth supporting device is mounted on the second end of the telescoping adjustable arm by a first arm and a second arm, the first arm extending in the first direction and the second arm extending in the vertical direction.

2. The dental imaging device of claim 1, wherein the plurality of attachment devices include a detachable patient head rest, and the plurality of attachment devices are configured to rotate along a horizontal axis corresponding with the plurality of attachment devices.

3. The dental imaging device of claim 2, wherein the detachable patient head rest is positioned at a first end of the adjustable patient positioning arm, the detachable patient chin rest is positioned at a second end of the adjustable patient positioning arm, and the detachable patient teeth supporting device is positioned in between the detachable patient head rest and the detachable patient chin rest.

4. The dental imaging device of claim 3, wherein a distance between the detachable patient head rest and the detachable patient teeth supporting device is adjustable based on the adjustable length of the adjustable patient positioning arm.

5. The dental imaging device of claim 3, wherein a distance between the detachable patient chin rest and the detachable patient teeth supporting device is adjustable based on the adjustable length of the adjustable patient positioning arm.

6. The dental imaging device of claim 2, wherein the detachable patient head rest is a head band to support a patient's head.

7. The dental imaging device of claim 1, wherein a detachable patient head rest frame is attached to the second end of the telescoping adjustable arm and the detachable patient head rest frame is configured to support a detachable patient head rest.

8. The dental imaging device of claim 1, wherein the adjustable patient positioning arm is in an upright position.

9. The dental imaging device of claim 1, wherein the image sensor is a digital camera, and the plurality of attachment devices are configured to move along the vertical direction.

10. A method of assembling a dental imaging device, the method comprising:

mounting an image sensor detachably on a first end of a telescoping adjustable arm, wherein the telescoping adjustable arm has an adjustable base a stationary member and a movable member slidably disposed within the stationary member, wherein the telescoping adjustable arm is configured to adjust an adjustable length of the telescoping adjustable arm by sliding the movable member within the stationary member, wherein an infrared sensor or an ultrasonic wave sensor is coupled to the adjustable base;

mounting an adjustable patient positioning arm directly on a second end of the telescoping adjustable arm, wherein a distance between the adjustable patient positioning arm and the image sensor in a first direction is adjustable based on an adjustable length of the telescoping adjustable arm in the first direction and wherein the telescoping adjustable arm includes a position indicator scale, the position indicator scale including a plurality of notches utilized for calibrating the distance in the first direction between the adjustable patient positioning arm and the image sensor;

the adjustable patient positioning arm comprising a plurality of attachment devices, wherein the plurality of attachment devices includes a detachable patient teeth supporting device, and a detachable patient chin rest; and the plurality of attachment devices on the adjustable patient positioning arm are positioned relative to the image sensor to capture an image of a patient's teeth, wherein the image sensor is adjustable in a vertical direction perpendicular to the first direction, and wherein the detachable patient teeth supporting device is mounted on the second end of the telescoping adjustable arm by a first arm and a second arm, the first arm extending in the first direction and the second arm extending in the vertical direction.

11. The method of claim 10, wherein the plurality of attachment devices include a detachable patient head rest, and the plurality of attachment devices are configured to rotate along a horizontal axis corresponding with the plurality of attachment devices.

12. The method of claim 11, wherein the detachable patient head rest is positioned at a first end of the adjustable patient positioning arm, the detachable patient chin rest is positioned at a second end of the adjustable patient positioning arm, and the detachable patient teeth supporting device is positioned in between the detachable patient head rest and the detachable patient chin rest.

13. The method of claim 12, wherein a distance between the detachable patient head rest and the detachable patient teeth supporting device is adjustable based on the adjustable length of the adjustable patient positioning arm.

14. The method of claim 12, wherein a distance between the detachable patient chin rest and the detachable patient teeth supporting device is adjustable based on the adjustable length of the adjustable patient positioning arm.

15. The method of claim 11, wherein the detachable patient head rest is a head band to support a patient's head.

16. The method of claim 10, wherein a detachable patient head rest frame is attached to the second end of the telescoping adjustable arm and the detachable patient head rest frame is configured to support a detachable patient head rest.

17. The method of claim 10, wherein the adjustable patient positioning arm is in an upright position.

18. The method of claim 10, wherein the image sensor is a digital camera, and the plurality of attachment devices are configured to move along the vertical direction.

* * * * *